United States Patent [19]

Ichikawa et al.

[11] 4,310,430
[45] Jan. 12, 1982

[54] α-OLEFIN-DIALKYLMALEATE-BASED LIQUID SEPARATING AGENT

[75] Inventors: Toshizi Ichikawa; Teruko Watanabe; Yoshimitus Asada, all of Tokyo, Japan

[73] Assignee: Terumo Corporation, Tokyo, Japan

[21] Appl. No.: 184,084

[22] Filed: Sep. 4, 1980

[30] Foreign Application Priority Data

Sep. 11, 1979 [JP] Japan .................................. 54-116388
May 26, 1980 [JP] Japan .................................. 55-69913

[51] Int. Cl.³ ...................... B01D 17/00; B01D 21/26; C09K 3/00
[52] U.S. Cl. ..................................... 252/60; 210/767; 210/782; 210/789; 210/927; 526/321
[58] Field of Search .................. 252/60; 210/927, 789, 210/516, 782, 767; 526/321

[56] References Cited
U.S. PATENT DOCUMENTS 4,172,803 10/1979 Ichikawa et al. ..................... 252/60

Primary Examiner—Dennis L. Albrecht
Attorney, Agent, or Firm—Frishauf, Holtz, Goodman & Woodward

[57] ABSTRACT

A liquid separating agent used for fractionating a liquid such as blood that contains more than one component of different specific gravities, by separating a specific component from other components by means of the specific gravity difference is characterized by consisting of as the main component an α-olefin-dialkylmaleate copolymer having a viscosity between 10,000 and 80,000 cp (at 25° C.); a viscosity and specific gravity adjusting agent such as silica or clay; and wax, a surfactant and so on as required.

10 Claims, 2 Drawing Figures

α-OLEFIN-DIALKYLMALEATE-BASED LIQUID SEPARATING AGENT

The present invention relates to a liquid separating agent used for separating components in liquids consisting of more than one component of different specific gravities.

This liquid separating agent is used to fractionate a specific component from other components using the specific gravity difference between the specific component and other components of a liquid to be fractionated and by being interposed between these components. For this purpose, it is desired that the liquid separating agent have a specific gravity between those of said components, be flowable during centrifugal separation, and not flowable and stable after the operation of centrifugal separation is completed.

A known conventional liquid separating agent of this kind is a gel-like material consisting of silicone oil, silica and a gelling agent. But a liquid separating agent of such a composition has problems. For example, because components which are mutually insoluble are mechanically mixed to obtain a thixotropic gel by means of a gelling agent which accelerates the formation of hydrogen bonds between the silica particles (specific gravity adjusting agent), coagulation develops due to this hydrogen bond growing stronger as time elapses, resulting in phase separation and poor buoyancy upon centrifugal separation. To prevent this, addition of a surfactant for avoiding phase separation has been proposed, but this presented another problem of hemolysis by the surfactant.

Further, liquid separating agents of the above composition have drawbacks such as the tendency to change their nature by cross-linking and other chemical changes upon γ-ray sterilization after encapsulation of a suitable quantity in a blood collecting tube. This degrades the liquid separating function, and delays blood coagulation and clot deposition by evaporation of low molecular components of the gel-like material rendering the inner surface of the tube water-repellent. Furthermore, these separating agents are fairly expensive due to particular raw materials being used.

Another known liquid separatng agent is a gel-like material of polyester base. This material is not necessarily satisfactory in that it renders the inner surface of the tube water-repellent resulting in delay of blood coagulation and clot deposition. Furthermore, liquid separating agents of this type smell unpleasant. It is frequently observed when a 7 cc blood sampling tube is used that the gel material fails to be sufficiently fluidized due to insufficient stress during the centrifusing operation owing to an insufficient amount of blood being sampled.

The present invention was made to eliminate these problems of the prior art and has for its object to provide a liquid separating agent that has excellent stability against change over long periods of time, can be subjected to γ-ray sterilization, show virtually no water-repellency, is free of unpleasant odors and can be manufactured at comparatively low cost.

To the above and other ends, the present invention provides a liquid separating agent for fractionating a liquid that contains more than one component of different specific gravities by separating a specific component by means of the specific gravity difference characterized by consisting of, as the main component, an α-olefin-dialkylmaleate copolymer having a viscosity between 10,000 and 80,000 cp, preferably between 40,000 and 80,000 cp (at 25° C.) and viscosity and specific gravity adjusting agents mixed therewith.

BRIEF DESCRIPTION OF THE DRAWINGS

This invention can be more fully understood from the following detailed description when taken in conjunction with the accompanying drawings, in which.

Figure 1:
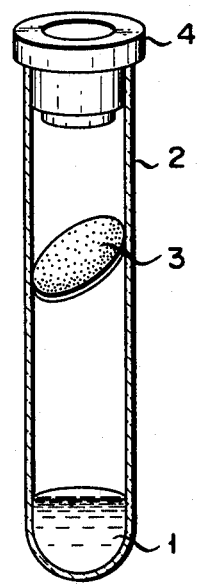
FIG. 1 is a perspective view illustrating the use of the liquid separating agent of the present invention as a blood serum separator encapsulated in a blood collection tube.

In the present invention, the α-olefin-dialkylmaleate copolymer has the general formula:

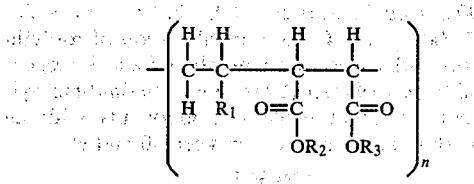

where $R_1$ stands for an alkyl group having 2 to 58 carbon atoms which in the copolymer molecule may either be the same kind or a combination of different kinds as desired; $R_2$ and $R_3$ are selected from the group consisting of methyl, ethyl, butyl, and 2-ethylhexyl groups; n is an integer which allows the viscosity of said copolymer to be in the range of 40,000 to 80,000 cp (at 25° C.) when using said copolymer as the main component.

This α-olefin-dialkylmaleate copolymer is light yellow in color, transparent, odorless, inert to blood, free of blood absorption, elution and so on, and stable for long periods of time. It allows the inner surface of the blood collecting tube to remain clean since it does not produce any water-repellent material. It does not substantially change its chemical or physical nature upon sterilization with gamma rays or the like.

When the liquid separation agent of the present invention is used for blood serum separation, the specific gravity of this α-olein-dialkylmaleate copolymer is selected between 1.00 and 1.038, preferably between 1.02 and 1.035.

According to the present invention, aliphatic amine derivatives of smectite clay may be aliphatic primary amine, aliphatic secondary amine or aliphatic tertiary amine derivatives of smectite clay. These amine derivatives are already known. Among these derivatives, aliphatic tertiary amine derivatives of smectite clay are most desirable, examples of which are Bentone 34, Bentone 38, Bentone 27, and Bentone 128 (quaternary ammonium salts of smectite clay, products of NL Industry CO.).

The inorganic fine powder used as the viscosity and specific gravity adjusting agent in the present invention may be suitably selected from calcined silica, precipitated silica and so on.

The structure-forming agent used in the present invention is added for maintaining the gel state of the liquid separation agent, and can be selected as desired according to the liquid to be fractionated. In the separation of blood serum, for example, dimethylpolysiloxane-polyoxyalkylene copolymer (e.g., trade names SH-3771, SH-190, and SH-192 of Toray Silicone Co., Ltd.) or Carbitol (e.g., ethyldiglycol) and the like may be used.

In the present invention, in addition to the α-olefin-dialkylmaleate copolymer, the viscosity and specific gravity adjusting agent and the structure-forming agent, a surfactant (e.g., polyoxyethylene-hydrogenated caster oil monolaurate, polyoxy-ethylene-hydrogenated caster oil tri-isostearate or the like) may be added as required.

Compositions of the liquid separating agent of the present invention for serum separation are shown in the following tables 1 and 2. In these tables, the α-olefin-dialkylmaleate copolymer (A) is an n-α-olefin-dimethylmaleate copolymer average molecular weight 3,000–4,000; specific gravity 1.027–1.038 (at 25° C.); viscosity 40,000–70,000 cp (25° C.) of a combination of α-olefin components with carbon atom numbers 12 and 14, respectively; the copolymer (B) is an n-α-olefin-dimethylmaleate copolymer average molecular weight 2,000–3,000; specific gravity 1.005 (28° C.); viscosity 10,000–15,000 cp (28° C.) of a combination of α-olefin components with carbon atom numbers 6 and 8, respectively; and the copolymer (C) is an n-α-olefin-dimethylmaleate copolymer of α-olefin components with an average carbon atom number between 30 and 60.

TABLE 1

(examples of serum separation agent compositions)

Unit: parts by weight

| Composition number | 1 | 2 | 3 | 4 | 5 | 6 |
|---|---|---|---|---|---|---|
| α-olefin-dialkylmaleate copolymer | | | | | | |
| (A) | 100 | 100 | 100 | 100 | 50 | — |
| (B) | — | — | — | — | 50 | 100 |
| (C) | — | — | 1.0 | 3.0 | — | — |
| Aerosil R-972* | — | — | 2.0 | 2.0 | 1.0 | — |
| Aerosil 200** | 1.0 | 1.0 | — | — | — | — |
| Benton 38*** | — | 1.0 | 1.0 | — | 1.0 | 3.0 |
| Benton 34*** | — | — | — | — | 1.0 | — |
| Benton 27*** | 3.0 | — | — | — | — | — |
| Benton 128*** | — | — | 2.0 | — | — | — |

*hydrophobic silica fine powder of average particle size 16 mμ, apparent specific gravity about 60 g/l, (product of NIPPON AEROSIL CO., LTD.)
**hydrophilic silica fine powder of average particle size 12 mμ, apparent specific gravity about 60 g/l, (product of NIPPON AEROSIL CO., LTD.)
***quaternary ammonium salts of smectite clay, (products of NL Industry CO., U.S.A.)

TABLE 2

(examples of serum separation agent compositions)

Unite: parts by weight

| Composition number | 7 | 8 | 9 | 10 | 11 | 12 |
|---|---|---|---|---|---|---|
| α-olefin-dialkylmaleate copolymer | | | | | | |
| (A) | 100 | 100 | 100 | 100 | 50 | — |
| (B) | — | — | — | — | 50 | 100 |
| (C) | — | — | 5.0 | 5.0 | — | — |
| Aerosil R-972* | 6 | — | 7.0 | 5.0 | 7.0 | 7 |
| Aerosil 200** | — | 6 | — | — | — | — |
| Surfactant*** | 0.5 | 1.0 | 1.0 | — | 1.0 | 3.0 |
| Structure-forming agent**** | 0.18 | 0.04 | — | 0.2 | 0.5 | 0.6 |

*see Table 1
**see Table 1
***Polyoxyethylene-hydrogenated caster oil monolaurate, (product of NIHON EMULSION CO., LTD.)
****SH-3771, (product of Toray Silicone Co., Ltd.), dimethylpolysiloxane-polyoxyalkylene copolymer with specific gravity 1.060–1.080 (20° C.) and viscosity 260–280 cp.

Next, the preparation method of the liquid separating agent of the present invention will be described.

First, the manufacturing method of the α-olefin-dialkylmaleate copolymer is low polymerization of ethylene to obtain an n-α-olefin. This is then separated into fractions of carbon atom numbers, for example, of 4, of 6, of 8 and 10, of 12 and 14, of 16 and 18, and of 30 to 60 by fractionating distillation. In accordance with the specific gravity of the liquid to be fractionated, these fractions may be used either singly or in combination, and a fraction with carbon atom numbers of 12 and 14, or of 6 and 8 is preferable for use in serum separation from the standpoints of viscosity and specific gravity. The selected fraction is subjected to copolymerization with a maleic diester in the conventional manner to obtain the desired product.

Using this α-olefin-dialkylmaleate copolymer with a viscosity between 10,000 and 80,000 cp, preferably between 40,000 and 80,000 cp (25° C.) as the base, an aliphatic amine derivative of smectite clay, a viscosity and specific gravity adjusting agent such as fine silica powder, a structure-forming agent and a wax consisting of an α-olefin-maleic-diester copolymer are aded as required. The mixture is kneaded using either a roll mill, a grinding mill, a planetary mixer or the like.

The liquid separating agent thus prepared should preferably has a viscosity, for use in serum separation for example, between 250,000 and 800,000 (25° C.) and a specific gravity between 1.035 and 1.055. All of the components in the previous tables are thixotropic, showing flowability upon application of a centrifugal force or the like and staying in the normal condition as a stable uniform gel otherwise. Furthermore, because this liquid separating agent does not contain a gelling agent such as those which are used conventionally, it is not apt to coagulate in time as stated previously, nor does it foster phase separation or deterioration of buoyancy. Its specific gravity is comparatively high being close to that of blood serum, so that even if phase separation does take place the base layer does not float suspended in the serum.

EXAMPLE

Figure 2:
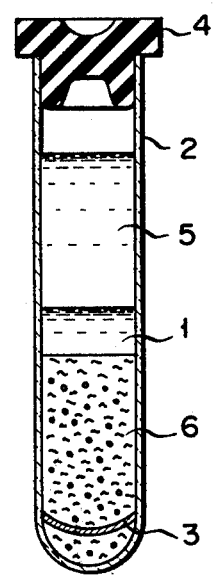
FIG. 2 is a sectional view of the blood collection tube shown in FIG. 1 after centrifugal separation.

As shown in FIG. 1, about 1.7 ml of each liquid separating agent composition 1 above (numbers 1 to 12) was put it the bottom of a 10 cc blood collecting tube 2. A polyester unwoven cloth 3 coated with 1–5 mg of diatomaceous earth (e.g., Caper Flattery Sand, trade name WG-200, for Kyoritsu Ceramic Materials Co., Ltd.) or micro-glass powder, was then placed at a slant in each blood collecting tube. Each tube was then stopped with a butyl rubber plug 4, and the tubes were placed under reduced pressure. Then a blood sample was placed in each blood collecting tube and allowed to stand for 7 to 8 minutes. As a result, the diatomaceous earth dispersed in the blood upon the introduction of the blood, and it accelerated blood coagulation together with the nonwoven cloth 3. Adequate coagulation was thus attained within this short time. Each blood collecting tube was placed in a centrifuge for 10 minutes at 700–1,000 G, and the liquid separating agent compositions were stably distributed between the serum and the clot layers. This state is shown in FIG. 2. Because the liquid separating agent is thixotropic and has a specific gravity between that of the blood serum 5 and that of the blood clots 6, it stays between the blood serum 5 and blood clot 6, forming a gel that separates these two layer. Since the diatomaceous earth and the unwoven cloth 3 have higher specific gravities, they were not included in the layer of blood serum 5. Thus, blood serum 5 obtained was of high purity with no entrainment of fibrin. This blood serum 5 was readily collected from the blood collecting tube by decantation or by suction.

Because the smectite clay particles are not light-transmitting, their state of dispersion can easily be checked by means of a microscope etc., making quality control easier. Because the aliphatic amine derivatives of smectite clay increase viscosity, the structure-forming agent which was conventionally essential can be eliminated. The use of wax in the above example is especially effective for prevention of phase separation of the liquid separating agent. Because the α-olefin-dialkylmaleate copolymer is used as the main component in the present invention, the manufacturing cost is very low, being about one third of that of liquid silicone.

When being used as a serum separator, the liquid separating agent does not form a water-repellent film in the blood collecting tube by releasing water-repellent substances and consequently does not cause delay of blood coagulation. Because the blood collecting tube is made of glass, it accelerates coagulation when contacting blood at the surface, so that it is necessary to keep the inner surface clean. Accordingly, compared with conventional liquid separating agents which have the drawback of forming a water-repellent film, the time needed for collecting blood serum is shortened. This is even more effective in combination with the use of the diatomaceous earth and unwoven cloth. The time saving can amount to as much as 30 minutes.

When encapsulation in a blood collecting tube is performed, sterilization is desirable. In clinical tests, no chemical or physical changes that cause adverse effects were found after applying gamma-ray sterilization.

In the above examples, use of the liquid separating agent of the present invention for serum separation was described, but it is to be understood that similar applications in other liquid separations are possible.

What we claim is:

1. A liquid separating agent for fractionating a liquid containing components of different specific gravities by separating a specific component by means of the specific gravity difference, characterized by consisting of, as the main component, a liquid α-olefin-dialkylmaleate copolymer having a specific gravity between 1.00 and 1.038 and the general formula

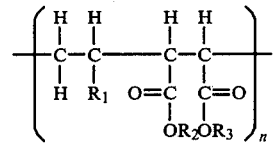

wherein
$R_1$ is an alkyl group having 2 to 58 carbon atoms which, in the copolymer molecule, may either be the same kind or a combination of different kinds; and $R_2$ and $R_3$ are selected from the group consisting of methyl, ethyl, butyl and 2-ethylhexyl groups; and n is an integer; and
at least one agent to control viscosity and specific gravity mixed therewith.

2. The liquid separating agent according to claim 1 wherein the α-olefin-dialkylmaleate copolymer has a viscosity between 10,000 and 80,000 cp (at 25° C.)

3. The liquid separating agent according to claim 1 wherein said agent to control viscosity and specific gravity are at least one element selected from the group consisting of aliphatic amine derivatives of smectite clay with carbon atom numbers between 8 and 24 and powdered silica.

4. The liquid separating agent according to claim 3 wherein said agent is selected from quaternary ammonium salts of smectite clay.

5. The liquid separating agent according to claim 3 wherein said powdered silica is calcined silica or precipitated silica.

6. The liquid separating agent according to claim 1 wherein $R_1$ in said general formula is a combination of alkyl groups having 10 and 12 carbon atoms.

7. The liquid separating agent according to claim 1 wherein $R_1$ in said general formula is a combination of alkyl groups having 4 and 6 carbon atoms.

8. The liquid separating agent according to claim 1 which also contains a structure-forming agent in an amount between 0.04 and 0.6 part by weight based on 100 parts by weight of said α-olefin-dialkylmaleate copolymer.

9. The liquid separating agent according to claim 1 which also contains 0.5 to 3.0 parts by weight of a surfactant based on 100 parts by weight of said α-olefin-dialkylmaleate copolymer.

10. The liquid separating agent according to claims 6 or 7 which also contains a structure-forming agent in an amount between 0.04 and 0.6 part by weight based on 100 parts by weight of said α-olefin-dialkylmaleate copolymer.

* * * * *